(12) United States Patent
Malin

(10) Patent No.: US 8,192,133 B2
(45) Date of Patent: *Jun. 5, 2012

(54) CLIMATE CONTROLLED CABINET WITH MOVABLE CARRIER

(75) Inventor: Cosmas G. Malin, Mauren (LI)

(73) Assignee: Liconic AG, Nendeln (LI)

( * ) Notice: Subject to any disclaimer, the term of this patent is extended or adjusted under 35 U.S.C. 154(b) by 19 days.

This patent is subject to a terminal disclaimer.

(21) Appl. No.: 12/414,335

(22) Filed: Mar. 30, 2009

(65) Prior Publication Data

US 2009/0245986 A1 Oct. 1, 2009

Related U.S. Application Data

(63) Continuation of application No. 10/738,222, filed on Dec. 18, 2003, now Pat. No. 7,510,362.

(30) Foreign Application Priority Data

Dec. 18, 2002 (CH) ...................................... 2172/02

(51) Int. Cl.
*B01F 11/00* (2006.01)
(52) U.S. Cl. ........................................ 414/283; 366/208
(58) Field of Classification Search .................. 414/277, 414/281, 282, 283; 366/208
See application file for complete search history.

(56) References Cited

U.S. PATENT DOCUMENTS

| 4,250,266 A | 2/1981 | Wada |
|---|---|---|
| 4,696,902 A | 9/1987 | Bisconte |
| 4,750,845 A * | 6/1988 | Nabetani ..................... 366/208 |
| 4,868,122 A | 9/1989 | Kominek et al. |
| 5,143,193 A | 9/1992 | Geraci |
| 5,266,272 A | 11/1993 | Griner et al. |
| 5,346,303 A | 9/1994 | Heinonen et al. |
| 5,449,229 A | 9/1995 | Aschenbrenner et al. |
| 5,470,744 A | 11/1995 | Astel |
| 5,733,024 A | 3/1998 | Slocum et al. |
| 5,735,587 A | 4/1998 | Malin et al. |
| 6,027,190 A | 2/2000 | Stewart et al. |
| 6,039,422 A | 3/2000 | Butters et al. |
| 6,129,428 A | 10/2000 | Helwig et al. |
| 6,228,636 B1 | 5/2001 | Higuchi |
| 6,323,035 B1 | 11/2001 | Kedar et al. |
| 6,475,776 B1 | 11/2002 | Higuchi |
| 6,478,524 B1 | 11/2002 | Malin |
| 6,536,859 B1 | 3/2003 | Bathe |
| 6,568,770 B2 | 5/2003 | Gonska et al. |
| 6,579,002 B1 | 6/2003 | Bartick et al. |
| 6,691,748 B1 | 2/2004 | Tajima |
| 7,338,199 B2 * | 3/2008 | Hafner ......................... 366/208 |
| 7,510,362 B2 * | 3/2009 | Malin ........................... 414/283 |
| 7,832,921 B2 * | 11/2010 | Malin ........................... 366/208 |

(Continued)

FOREIGN PATENT DOCUMENTS

CH 690 645 11/2000

(Continued)

*Primary Examiner* — Charles A Fox
(74) *Attorney, Agent, or Firm* — Greenblum & Bernstein, P.L.C.

(57) ABSTRACT

A climate-controlled cabinet that includes a climate-controlled chamber for receiving a storage system, a carrier arranged in said chamber, and at least one storage tower arranged in said chamber and mounted to the carrier. The storage tower includes a plurality of locations for objects to be stored. A transport device is included for automatically transporting objects between the storage tower and an external system, and a shaker for automatically shaking the carrier.

3 Claims, 4 Drawing Sheets

U.S. PATENT DOCUMENTS

2003/0215367 A1  11/2003  Fitzgerald et al.

FOREIGN PATENT DOCUMENTS

| | | |
|---|---|---|
| DE | 198 57 282 A1 | 6/2000 |
| EP | 0 154 536 A2 | 9/1985 |
| EP | 0 293 782 A1 | 12/1988 |
| EP | 0 569 214 A2 | 11/1993 |
| EP | 1 074 488 A1 | 2/2001 |
| EP | 1 256 808 A1 | 11/2002 |
| EP | 1 354 623 A1 | 10/2003 |
| FR | 2 788 042 A1 | 7/2000 |
| WO | 92/14550 A1 | 9/1992 |
| WO | 93/09440 A1 | 5/1993 |
| WO | 98/05753 A1 | 2/1998 |
| WO | 99/15905 A1 | 4/1999 |
| WO | 02/059251 A2 | 8/2002 |

* cited by examiner

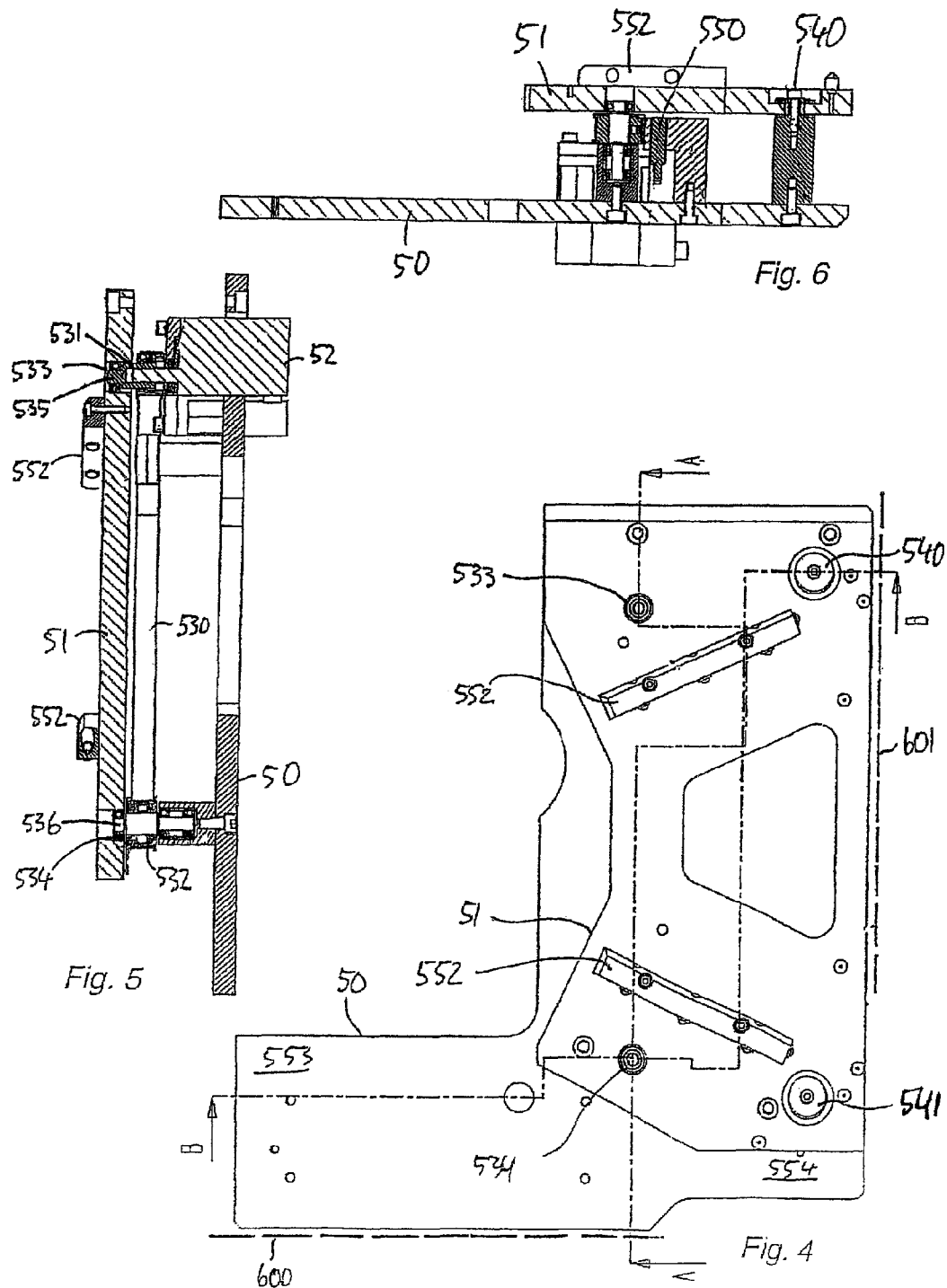

CLIMATE CONTROLLED CABINET WITH MOVABLE CARRIER

CROSS REFERENCE TO RELATED APPLICATIONS

This application is a Continuation of U.S. patent application Ser. No. 10/738,222 filed Dec. 18, 2003 now U.S. Pat. No. 7,510,362, and claims the priority of Swiss application 2172/02, filed Dec. 18, 2002, the disclosures of which are expressly incorporated herein by reference herein in their entireties.

BACKGROUND OF THE INVENTION

1. Field of the Invention

The invention relates to a climate-controlled cabinet. Such cabinets comprise a climate-controlled chamber for receiving objects to be stored and a climate controller for generating controlled, climatic conditions in this chamber. They are used for objects that must be stored under controlled climatic conditions. The field of applications of such cabinets ranges from the long-term storage of microtiterplates to the breeding of cell cultures or microorganisms under well defined climatic conditions in a clean environment. In applications where particles or micro microorganisms must be stored floating in a solvent, an agitation of the stored goods may be necessary.

2. Discussion of Background Information

CH 690 645 describes a device having a user door and an automatic auxiliary door with storage towers and a transport device inside, the latter for transporting the objects between the storage towers and the auxiliary door. This arrangement has the disadvantage that the transport device makes access to the inner floor and walls of the chamber difficult or even impossible. For cleaning, the transport device must be removed.

The device shown in DE 100 24 581 has an inclined floor and a raised transport device. Accessibility of the floor is, however, still not satisfactory. The lateral walls and the back wall remain difficult to reach. The raised transport device leads to a waste of space.

SUMMARY OF THE INVENTION

Hence, the embodiments of the present invention provide a climate-controlled cabinet that is easy to clean.

In order to achieve the foregoing and still further aspects, a climate-controlled cabinet is provided that comprises a climate-controlled chamber for receiving a storage system, a carrier arranged in said chamber, at least one storage tower arranged in said chamber and mounted to said carrier, said storage tower comprising a plurality of locations for objects to be stored, and a transport device for automatically transporting objects between said storage tower and an external system, wherein said carrier is movable in respect to said chamber.

By designing the carrier to be movable, it can be moved when access is required to the walls below and/or behind it.

In a further aspect of the invention, a climate-controlled cabinet is provided that can be used for a very wide range of goods.

According to the above-noted further aspect, a climate-controlled cabinet is provided that comprises a climate-controlled chamber for receiving a storage system, a carrier arranged in said chamber, at least one storage tower arranged in said chamber and mounted to said carrier, said storage tower comprising a plurality of locations for objects to be stored, and a transport device for automatically transporting objects between said storage tower and an external system, and a shaker for automatically shaking said carrier.

In this embodiment, the shaker keeps the goods agitated, thereby even allowing the storage of goods that must be stirred.

Embodiments of the invention are directed to a climate-controlled cabinet that includes a climate-controlled chamber for receiving a storage system, at least one storage tower arranged on a carrier in said chamber and mounted to said carrier, said storage tower comprising a plurality of locations arranged vertically above each other for receiving objects to be stored, a transport device for automatically transporting objects between said storage tower and an external system, and a shaker for automatically shaking said carrier without rotating said carrier.

Embodiments of the invention are directed to a climate-controlled cabinet that includes a climate-controlled chamber for receiving a storage system, at least one storage tower arranged on a carrier in said chamber and mounted to said carrier, said storage tower comprising a plurality of locations arranged vertically above each other for receiving objects to be stored, a transport device for automatically transporting objects between said storage tower and an external system, and a shaker for automatically shaking said carrier. The shaker includes a plurality of rotating bodies, each rotating body having a center, being rotatable about said center and having a peg arranged eccentrically in respect to said center, wherein said pegs engage said carrier for shaking said carrier when said rotating bodies are rotated about said centers.

According to features of the embodiments the rotating bodies can be pinions.

Embodiments of the invention are directed to a climate-controlled cabinet that includes a climate-controlled chamber for receiving a storage system, at least one storage tower arranged in said chamber, said storage tower comprising a plurality of locations for objects to be stored, a transport device for automatically transporting objects between said storage tower and an external system, and a shaker structured and arranged to impart a shaking motion to the at least one storage tower.

In accordance with still yet other features of the embodiments, a shakeable carrier can be arranged within the climate-controlled chamber. The at least one storage tower can be positionable on the shakeable carrier. Further, the shaker can be coupled to the shakeable carrier, and may be structured and arranged to shake the carrier in a horizontal direction. The shaker can include a drive structured and arranged to tilt the at least one tower. Also, the shaker can include a drive structured and arranged to rotate the shakeable carrier. The shaker may be structured and arranged to bring the shakeable carrier into a vortex motion.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 4 is a top view of a carrier plate and base plate of a device for two storage towers, FIG. 5 is a sectional view along line A-A of FIG. 4; and FIG. 6 is a sectional view along line B-B of FIG. 4.

DETAILED DESCRIPTION OF THE INVENTION

Figure 1A:
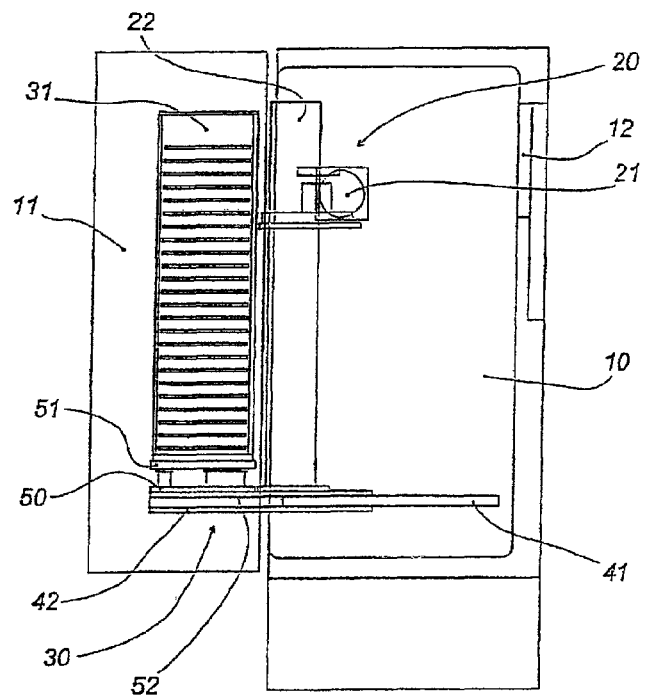
FIG. 1a is a lateral view of a first embodiment of a climate-controlled cabinet with displaceable storage system.

FIG. 1 shows a climate controlled cabinet having a climate controlled chamber 10. A storage system 30 is arranged inside climate controlled chamber 10. Storage system 30 comprises at least one storage tower 31 having a plurality of locations arranged vertically above each other for receiving objects to be stored and can be removed as a whole from the chamber. Advantageously, several storage towers 31 are provided. Storage system 30 further comprises a transport device 20 for automatically transporting objects between the storage tower 31 and an external system. Transport device 20 can be displaced horizontally and vertically and can be pivoted about a vertical axis. It can access all storage locations of all storage towers and pass the objects through an auxiliary door 12. A corresponding device is described in CH 690 645.

The small auxiliary door 12 is arranged at a back wall of climate controlled chamber 10. Transport device 20 passes the objects through this auxiliary door. For manual access to the storage towers, a large front door 11 is arranged in a front wall of chamber 10.

A base plate 50 is arranged inside chamber 10 and carries an elevator 22 with transport lift 21 of transport device 20. It also carries a carrier plate 51. Base plate 50 is advantageously a U-shaped metal plate having legs parallel to the side walls and a base parallel to and along the back wall, but other designs, as described below, can also be used.

The storage towers 31 are arranged on carrier plate 51, i.e. carrier plate 51 serves as a carrier for the storage towers.

Carrier plate 51 can be moved horizontally in respect to base plate 50 by a translational drive 52. Base plate 51 is arranged on carriages 42 running in tracks 41, i.e. carriages 42 and tracks 41 form a guide for guiding base plate 50 in its horizontal movement in respect to chamber 10. The tracks 41 are mounted horizontally to the side walls of chamber 10 in such a manner that the storage system can be moved through user door 11 and out of chamber 10. Carrier plate 51 is mounted to tracks 41 in such a way that it can be moved through door 11 and out of chamber 10. By pulling the transport system out of the chamber, the whole chamber and in particular its floor become accessible. At the same time, maintenance and control work on the transport system is simplified by the improved accessibility.

The horizontal movability of carrier plate 51 in respect to base plate 50, can, e.g., also be used to implement a shaking motion of the storage towers.

Figure 1B:
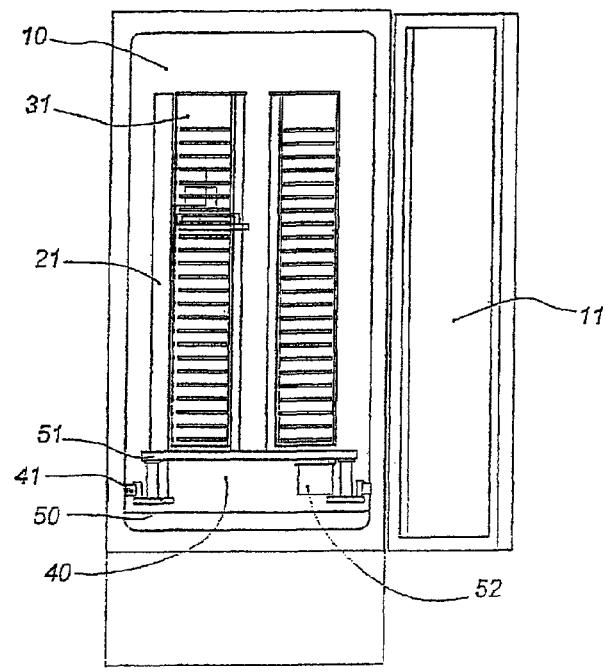
FIG. 1b is a front view of the first embodiment.

FIG. 1b shows a front view of the device. Base plate 50 is designed such that, together with carrier plate 51, it forms a bridge 40. For this purpose, carrier plate 51 is arranged on the lateral legs of base plate 50 therebelow by supports such that a freely accessible space below bridge 40 is formed. The bridge simplifies access to the floor of chamber 10 without increasing the height of the device.

Figure 2A:
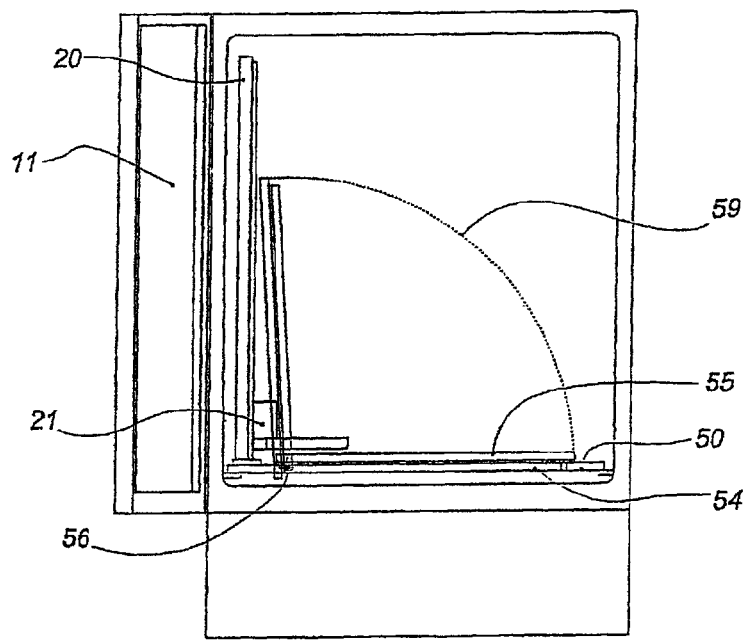
FIG. 2a is a front view of an embodiment of a climate-controlled cabinet with partially pivotal storage system.

FIG. 2a shows an embodiment where carrier plate 51 is mounted to a pivoting bearing and can be pivoted about a pivot axis 56. Pivot axis 56 advantageously extends horizontally and is perpendicular to the front door opening of the climate controlled cabinet. A rotating table 55 is arranged on support plate 51. Rotating table 55 serves to receive the storage towers 31. Carrier plate 51 is in a common plane with base plate 50 and pivotal axis 56 extends through base plate 50. When tilting carrier plate 51 about a tilting angle 59, an opening is formed in base plate 50, which provides access to the floor of chamber 10. In this embodiment, accessibility does not come at the expense of additional device height. In order to be able to tilt carrier plate 51 into the nearly vertical position shown in FIG. 2a, the storage towers 31 have to be removed from the cabinet.

Figure 2B:
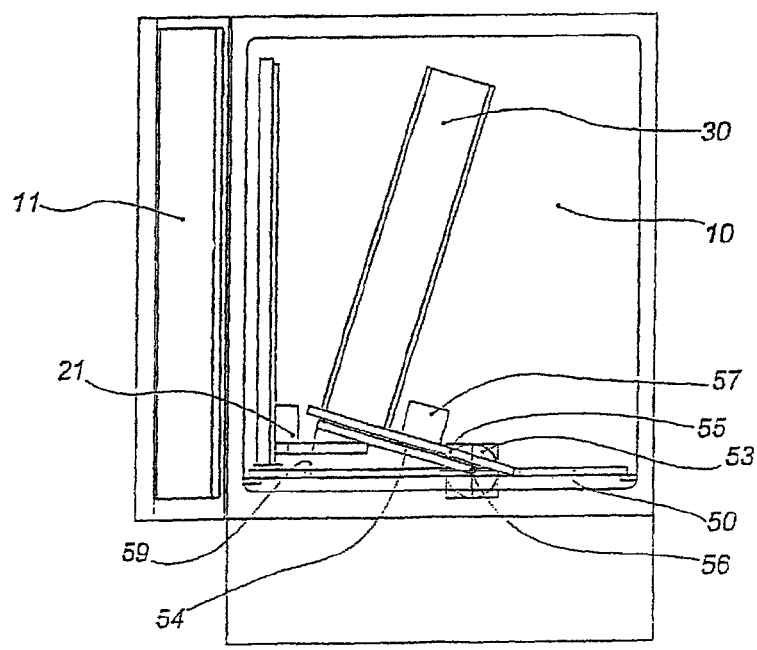
FIG. 2b is a front view of an embodiment of a climate-controlled cabinet with partially tiltable storage system.

FIG. 2b shows another embodiment having a pivotal or tiltable carrier plate 51. In this embodiment, the tilting motion of carrier plate 51 is carried out by a pivoting drive 53. In addition, a drive 57 is provided on carrier plate 51 for setting rotating table 55 into motion. With this embodiment of the cabinet, the objects to be stored can be stirred by tilting carrier plate 51 about a small angle (in order to bring the storage towers 31 into a slightly oblique position) and then activating drive 57 to rotate table 55.

Figure 3:
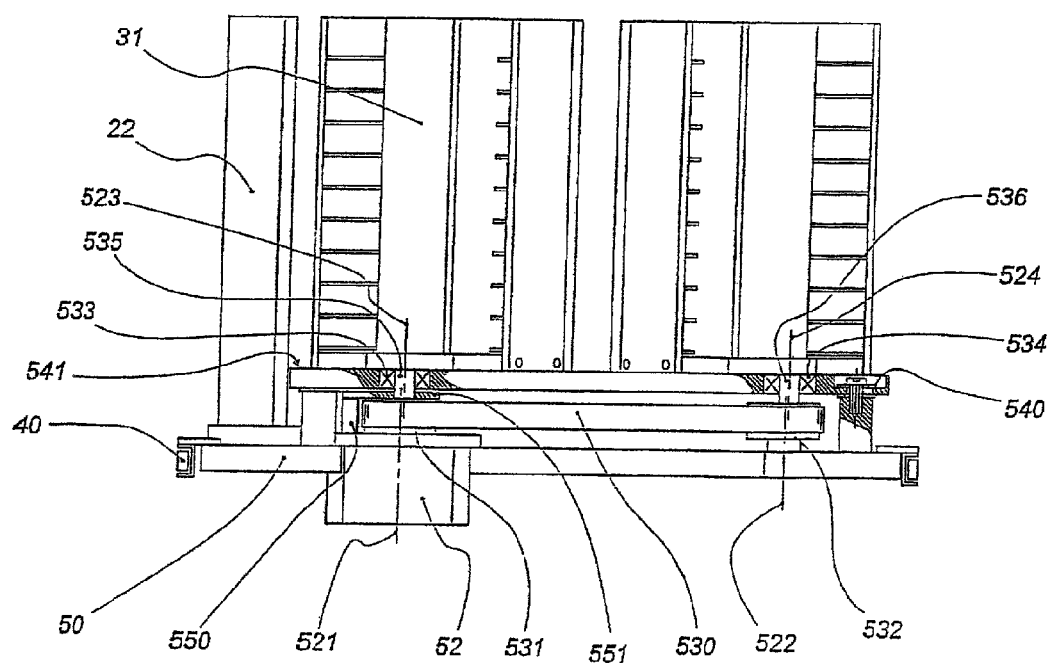
FIG. 3 is a complete view of an embodiment of a climate-controlled cabinet with a partially displaceable storage system.

FIG. 3 shows a detailed view of a further embodiment of a device with movable carrier plate 51. In this embodiment, the cabinet is designed to shake the storage towers and therefore contents of the objects to be stored.

Carrier plate 51 is mounted to stationary base plate 50 by way of two frictional bearings 540, 541 and by way of two peg bearings 533, 534. A pinion is arranged below each peg bearing. Each pinion has a peg 535, 536 arranged eccentrically in respect to the center of the pinion and extending into the respective bearing above it. A timing belt 530 runs around the pinions. One pinion 531 is coupled to the shaft of a drive 52, while the other pinion 532 is driven by a timing belt 530. When the pinions 531, 532 are rotated, carrier plate 51 is brought into a vortex motion by the pegs 535, 536, i.e. it is being shaken. The frictional bearings 540, 541, which prevent excessive loads on the peg bearings 533, 534, are designed such that carrier plate 51 can follow the motion. The amplitude of the vortex motion corresponds to the double distance of the axis of the pinions 521, 522 and the centers of the peg bearings 523, 524.

Elevator 22 does not follow the shaking motion. In order for it to access the storage locations in the storage towers 31, it needs, however, to be in a predefined position thereto. For this purpose, a position sensor 550 is arranged on base plate 50. It serves to measure the current position of carrier plate 51 (or, equivalently, the rotational position of one of the pinions) and drive 50 (which is e.g. a stepper motor) is controlled to move the pinions to a predefined angular position when stopping. In this manner, a known, i.e. defined relative position between the storage towers 31 and the transport device 20 and chamber 10 can be established such that transport device 20 can access the storage locations.

Carrier plate 51 can also be designed as the base plate of a carousel or it can support a carousel, wherein the storage towers are arranged in the carousel.

FIGS. 4 through 6 show a specific embodiment of a base plate 50 and a carrier plate 51 of a device with two storage towers and shaking mechanism, wherein the parts corresponding to those of FIG. 3 carry the same reference numerals. In addition to FIG. 3, it can be seen that attachment bars 552 are mounted to carrier plate 51. They serve to attach the two storage towers. FIGS. 4 through 6 also show a substantially L-shaped base plate 50, having one leg 553 extending parallel to a side wall 600 and a base member 554 parallel to front wall 601 of chamber 10, thereby providing good floor access. Transport device 20, which is mounted to leg 553, is not shown.

While there are shown and described presently preferred embodiments of the invention, it is to be distinctly understood that the invention is not limited thereto but may be otherwise variously embodied and practiced within the scope of the following claims.

What is claimed:

1. A climate-controlled cabinet comprising:
   a climate-controlled chamber for receiving a storage system;
   at least one storage tower arranged in said chamber, said storage tower comprising a plurality of locations for objects to be stored;
   a transport device for automatically transporting objects between said storage tower and an external system;
   a shaker structured and arranged to impart a shaking motion to the at least one storage tower;
   a shakeable carrier arranged within the climate-controlled chamber, wherein the at least one storage tower is positionable on the shakeable carrier,
   wherein the shaker is coupled to the shakeable carrier and wherein the shaker comprises a drive structured and arranged to tilt the at least one tower.

2. The climate-controlled cabinet of claim 1, wherein the shaker comprises a drive structured and arranged to rotate the shakeable carrier.

3. A climate-controlled cabinet comprising:
   a climate-controlled chamber for receiving a storage system;
   at least one storage tower arranged in said chamber, said storage tower comprising a plurality of locations for objects to be stored;
   a transport device for automatically transporting objects between said storage tower and an external system;
   a shaker structured and arranged to impart a shaking motion to the at least one storage tower;
   a shakeable carrier arranged within the climate-controlled chamber, wherein the at least one storage tower is positionable on the shakeable carrier,
   wherein the shaker is coupled to the shakeable carrier and wherein the shaker is structured and arranged to bring the shakeable carrier into a vortex motion.

* * * * *